(12) United States Patent
Nilsson et al.

(10) Patent No.: US 10,846,630 B2
(45) Date of Patent: Nov. 24, 2020

(54) PRIORITIZATION SYSTEM FOR MULTIPLE DISPLAYS

(71) Applicant: Ascom Sweden AB, Gothenburg (SE)

(72) Inventors: Magnus Nilsson, Stora Höga (SE); Linnea Fogelmark, Gothenburg (SE)

(73) Assignee: ASCOM SWEDEN AB, Gothenburg (SE)

( * ) Notice: Subject to any disclaimer, the term of this patent is extended or adjusted under 35 U.S.C. 154(b) by 398 days.

(21) Appl. No.: 15/493,888

(22) Filed: Apr. 21, 2017

(65) Prior Publication Data

US 2017/0228682 A1 Aug. 10, 2017

Related U.S. Application Data

(63) Continuation of application No. PCT/SE2015/051054, filed on Oct. 6, 2015.

(30) Foreign Application Priority Data

Oct. 23, 2014 (SE) ...................... 1451273

(51) Int. Cl.
| | |
|---|---|
| *G06Q 10/06* | (2012.01) |
| *G16H 40/20* | (2018.01) |
| *G06Q 50/22* | (2018.01) |
| *H04W 4/21* | (2018.01) |
| *H04W 4/12* | (2009.01) |

(52) U.S. Cl.
CPC ..... *G06Q 10/063112* (2013.01); *G06Q 10/06* (2013.01); *G06Q 50/22* (2013.01); *G16H 40/20* (2018.01); *H04W 4/21* (2018.02); *H04W 4/12* (2013.01)

(58) Field of Classification Search
CPC .......... G06Q 10/06; G06Q 10/063112; G06Q 50/22; G06F 19/00; G16H 40/20; H04W 4/02; H04W 4/12; H04W 4/21
See application file for complete search history.

(56) References Cited

U.S. PATENT DOCUMENTS

| | | | |
|---|---|---|---|
| 2003/0149598 A1 | 8/2003 | Santoso et al. | |
| 2005/0021369 A1 | 1/2005 | Cohen et al. | |
| 2006/0277070 A1 | 12/2006 | Hungerford et al. | |
| 2007/0044539 A1* | 3/2007 | Sabol ..................... | G06Q 10/06 73/19.01 |
| 2008/0164998 A1 | 7/2008 | Scherpbier et al. | |
| 2008/0312983 A1* | 12/2008 | Chakka .................. | G06Q 10/06 705/7.28 |
| 2011/0320230 A1 | 12/2011 | Podgurny et al. | |
| 2012/0041767 A1* | 2/2012 | Hoffman ................ | G06Q 50/22 705/1.1 |
| 2012/0290977 A1* | 11/2012 | Devecka ................ | G06Q 10/10 715/810 |
| 2014/0132481 A1 | 5/2014 | Bell et al. | |

* cited by examiner

*Primary Examiner* — Davoud A Zand
(74) *Attorney, Agent, or Firm* — Gabriela B. Tomescu, Esq.; Bergenstråhle & Partners AB

(57) ABSTRACT

A prioritization system in a communication network comprising multiple communication devices adapted to communicate sets of information through the communication network. The sets of information are each associated to a level of urgency and the prioritization system is adapted to prioritize the sets of information based on said levels of urgency. The prioritization system comprises at least one personal communication device associated to an individual user in the prioritization system and the individual user is further associated to a first and a second display.

11 Claims, 14 Drawing Sheets

PRIORITIZATION SYSTEM FOR MULTIPLE DISPLAYS

This application is the continuation of International Application No. PCT/SE2015/051054, filed 6 Oct. 2015, which claims the benefit of Swedish Patent Application No. SE 1451273-5, filed 23 Oct. 2014, the entire contents of which are hereby incorporated by reference.

TECHNICAL FIELD

The present invention relates generally to a prioritization device, method, and system for prioritization of information within a communication network.

BACKGROUND ART

Information flows and the amount of information exchange between different sorts of communication devices is constantly increasing both in professional and private application areas. The increased amount of data has created an ever growing need to sort among information and adapt a selective approach in relation to taking actions based on said information. In commercial applications and especially in professions wherein alerts, messages, tasks, and similar sets of information are distributed through communication devices this is an ever present problem. Information distributed to communication devices during a work shift indicating different work assignments that the personnel need to attend to with different urgency is becoming significantly more developed. This development further adds to the problem due to the increased amount of information included in such communications.

In clinical environments, such as hospitals, treatment centers, and other healthcare facilities, communication amongst personnel in different work functions is important and in many cases a lifesaving function that coordinates resources depending on patient needs. Doctors, nurses, and other personnel at such facilities often communicate through mobile devices such as pagers, tablets, general purpose computers, personal digital assistants (PDAs), or other devices that handles one or more of alarms, task assignments, messages, alerts, and voice calls.

Within the healthcare industry the communicated information have different urgency rates, despite the importance that the right decisions are made regarding priority of information many prior art solutions rely on the individual user to manually sort among the received information. This is partly due to that the solutions in prior art for clinical environments are different sorts of pagers that provide information to users by receiving and presenting information. The information is communicated from an alarm system and directed to personnel within the facility from either another member of the staff or a medical sensor communication device attached to a patient. According to state of the art technology, alerts, messages, and other information are put in a queue based on the importance of the information. For example, an alarm intended to inform the healthcare professional about an event not requiring an action is granted less priority than an emergency alarm from a co-worker.

However, the increased amount of information for each situation, possibly including for example video, live data, images, etc, in combination with the increased amount of alarms might create problems wherein the queue over a shift is constantly increasing and the less important issues might in a worst case scenario be postponed over and over again.

SUMMARY OF INVENTION

An object of the present invention is to provide a prioritization system that can prioritize information based on urgency, position, availability as well as presenting information through different displays depending on urgency, user identity, where the physical position is, and the availability of said user.

Thus the invention generally relates to a prioritization system in a communication network comprising multiple communication devices adapted to communicate sets of information through said communication network. The sets of information are each associated to a level of urgency and the prioritization system is adapted to prioritize the sets of information based on said levels of urgency. In the prioritization system, at least one of said communication devices is a personal communication device associated to an individual user in the prioritization system and the individual user is further associated to a first and a second display, and each personal communication device is associated to a list of qualifications in the prioritization system that are corresponding to the professional qualifications of the individual user associated to said personal communication device, each set of information communicated through said communication network is associated to a desired set of professional qualifications, the prioritization system is adapted to compare the desired set of professional qualifications with the set of professional qualifications associated to each personal communication device, the prioritization system is adapted to select the most suitable personal communication device associated to the most suitable set of professional qualifications and communicate the set of information to said personal communication device.

In one embodiment of the prioritization system the communication network is a general purpose data communication network, such as a WiFi, Bluetooth, GSM, 3G, LTE, or any other form of suitable network that can or may be used for communication of data, voice, alerts, or text. It is understood that the communication network in one embodiment can be a private communication network delimited to, for example, a specific organization, building, or otherwise delimited geographical or juridical area. However, the communication network could in another embodiment be a general purpose network, including but not limited to, telecommunication or data communication networks. It is further understood that the communication network can be wireless, non-wireless, or any combination thereof. However, in a preferred embodiment of the invention the communication network is a radio communication network.

Through the communication network are sets of information communicated between communication devices. Sets of information can be any form of information, such as alerts, messages, video, images, voice, tasks, alarms, or any other form of communication that can be communicated through a communication network. Sets of information are in one preferred embodiment limited sets of information comprising delimitations of time, size, length, or any other form of delimitations differentiating said sets of information from continuous broadcasts, such as commercial radio channels, TV-channels, or similar. The communication is in one embodiment conducted between different users of the communication network, however this is a non-limiting embodiment, to the prioritization system, communication could additionally be conducted between devices, such as medical devices attached to a patient, and individual users, or communication devices associated to individual users. The individual users are in a preferred embodiment of the invention healthcare professionals, such as doctors, nurses, or any other form of professional staff working in a healthcare providing environment.

The prioritization system could be any form of system, such as distributed, local on a server, or out-sourced in for example a cloud service that is adapted to conduct prioritizations among sets of information communicated through the aforementioned communication network.

In one embodiment of the prioritization system for a communication network the communication network comprises one or more communication devices, such as cell phones, PDA's, pagers, TV-screens, general purpose computers, or any other form of communication devices. The communication devices are for example personal communication device that are associated to an individual user, public communication devices that are associated to specific locations, teams, or specific areas of expertise, or any other form of communication device. In one embodiment is a personal communication device a communication device, such as a phone, comprising a processor, a memory, at least one screen, and an, in the prioritization system stated, association to a specific individual user.

The person skilled in the art understands that a single personal communication device at any given time can only be associated to one individual user, however for example during different shifts a single personal communication device could be associated to more than one specific user through for example a logon screen wherein the individual user signs in. Note that such a solution would only allow one active individual user at any given time.

Public communication devices are in a preferred embodiment TV-screens, monitors, or any other form of displays that can be arranged in a public environment, in for example a hospital area.

The display as described herein is in one embodiment a screen, for example the screen of a smartphone, PDA, tablet, or any other form of portable or stationary communication device. However, in another embodiment of the invention the display is part of a screen, for example in the public communication device wherein a monitor might constitute the first or second display for multiple users through divided fields. The person skilled in the art understands that a display can be any form of visualization arrangement illustrating text messages, numeric messages, video messages, images, or any combination thereof. A display thereby is any form of dynamic visual arrangement changing both appearance and presented information by means of electrical impulses, signals, or any other form of information carrier. It should however be noted that for the purpose of the prioritization system as described herein said first and second displays can in a preferred embodiment be arranged on the same physical device.

In one embodiment of the invention each individual user, being for example a healthcare professional or any other form of user of a communication device, is associated to a first and a second display. The first and second display is in one embodiment two different displays arranged on the same communication device. In another embodiment said displays are two separate displays associated to the same individual user but arranged on separate communication devices. One example of this is for example an individual user having a traditional pager, constituting the first display, and in addition has access to a public communication device constituting the second display arranged for example in a rest area, in the alley way, corridor, or any other place where the individual user often would pass through. In one preferred embodiment the first display could be a general purpose computer or a tablet.

In another embodiment of the invention is the second display one or more displays arranged around the working area of an individual user. For example, an individual user working in a healthcare environment could in one embodiment be stationary on a specific level or floor of a building. Arranged on multiple spots at this level or floor do multiple displays constitute the second display for at least one individual user. When moving around the individual user can always find information about the next task on said second display. In order to receive more information the individual user also have access to a second display, such as a tablet, PDA, or smartphone which provide additional information such as live video, EKG information, or any other form of live information that would provide useful information for the individual user responding to a set of information.

Each personal communication devices is in a preferred embodiment associated to a list of qualifications in the prioritization system. The list of qualifications corresponds to professional qualifications, skills, knowledge, education level, of the individual user. The set of qualifications may appear different depending on the application area and the person skilled in the art understands that the set of qualifications can be any form of list, database, or information set that describes the ability of an individual to perform one or more tasks, answer a question, or any other form of knowledge.

The person skilled in the art further understands that the comparison between the set of qualifications associated to an individual user and the desired set of professional qualifications may be any form of comparison. For example, in one embodiment of the invention an exact match is required; in another the most suitable individual user is identified.

In one embodiment of the invention the prioritization system in addition to selecting the most suitable personal communication device to communicate information to also creates a selection of which priority the individual user is required to read this information with. For example, if the situation that the information refers to is urgent and needs immediate attention the information is provided to a second display. In another situation wherein the information is urgent but not top priority the information can be displayed on the first display.

The first and second displays are in one embodiment further adapted to show information of different priority from the same set of information. The sets of information in such an embodiment comprise two levels of information providing different type of data to the individual user. For example, the prioritization system determines that the certain set of information shall be communicated to an individual user associated to a first and/or second screen. This particular set of information is for the purpose of describing one embodiment of the invention an alarm from a respiratory system. Said set of information comprises two different levels of information wherein a first level is the alarm notifying the individual user to respond to said alarm. The second level of information is a snippet of for example a respiratory curve as currently sent from a medical device attached to a patient associated to said set of information/alarm.

Said two different levels of information comprises information that are needed by the individual user at different stages in the process of responding to said set of communication. For example, one level comprise the information that an emergency is taking place requires the immediate attention of the individual user and is thereby presented on a second display associated to said individual user. The information comprising respiratory curve is important for the diagnostics and action to be performed by the individual user, however it is not important in relation to enable the individual user to start moving towards the physical location where the action is required. The second level of information is thereby presented on said first display that the individual user can access when he or she finds suitable in relation to the course of events corresponding to the communicated set of information.

In one embodiment, the prioritization system is further adapted to determine the physical location of each personal communication device, and the prioritization system is adapted to additionally consider said physical location when determining the most suitable personal communication device. All types of communication devices are in one embodiment enabled to facilitate the determination of their position.

For many application areas information communicated over the communication network mainly comprises information about actions, tasks, or alarms that the receiving individual user need to respond to. It is thereby important that in addition to selecting the most suitable individual user for the response qualification wise to select an individual with a physical location nearby the physical location where the response is required.

In one embodiment, the prioritization system is further adapted to determine the availability of the individual user associated to each personal communication device, and wherein the prioritization system is adapted to additionally consider said availability when determining the most suitable personal communication device.

In order to estimate the response time of an individual user in relation to a physical location both the physical location of said individual and the individuals availability is relevant.

In one embodiment of the prioritization arrangement the communication network is a communication network in a healthcare environment.

In one embodiment of the prioritization arrangement at least one of the communication devices is a public communication device, such as a monitor or TV-screen, associated to at least an individual user, preferably a team of healthcare professionals.

In one embodiment of the prioritization system the first and second displays are display sections of at least one screen. I.e. one screen can in one embodiment constitute the first and/or second display for more than one individual user, for example in the case of a public communication device.

In one embodiment of the prioritization system the first and second displays are arranged on the personal communication device and the displays are arranged on different geometrical facets of said personal communication device.

In one embodiment of the personal communication device is the first display arranged on a front side of said communication device and said second display is arranged, substantially perpendicular to said front side, on a top side of said communication device.

This means that the information presented on the second display can be viewed from above when the communication device for example is correctly placed in the pocket of an individual user. I.e. when the mobile communication device is tucked in to a pocket, the second display can still be viewed either through the opening in the pocket or if the mobile communication device is extending out through the opening of the pocket.

In one embodiment of the prioritization system the communication network is a peer-to-peer network.

The communication network is the network wherein the sets of information to be prioritized by the prioritization system are communicated. In different embodiments this communication network may have different characteristics. For example, in one embodiment of the prioritization system the communication network is a distributed communication network wherein each, or some of, the communication device of the network are peers in a peer-to-peer network. In another embodiment of the invention the communication network is a centralized network with a centralized node, for example a server, that handles the communication in said communication network.

In one embodiment of the prioritization system the prioritization system is part of a back-end system, such as a server.

In one embodiment is the prioritization system further adapted to allow a super user to manually intervene with the prioritizations, and wherein the prioritization system is adapted to additionally consider said manual interventions when determining the most suitable personal communication device.

The person skilled in the art understands that in different embodiments of the prioritization system different individual users, such as supervisors, super users, administrators, and regular users, may have different permissions in relation to for example manually intervene with sets of information and priorities thereof.

According to an aspect of the prioritization system for a communication network comprising multiple communication devices adapted to communicate sets of information through said communication network, the sets of information is each associated to a level of urgency and the prioritization system is adapted to prioritize the sets of information based on said levels of urgency. In the prioritization system is further at least one of said communication devices is a personal communication device associated to an individual user in the prioritization system, said individual user is further associated to a first and a second display, and
- each personal communication device is associated to a list of qualifications in the prioritization system that are corresponding to the professional qualifications of the individual user associated to said personal communication device,
- each set of information communicated through said communication network is associated to a desired set of professional qualifications,
- the prioritization system is adapted to compare the desired set of professional qualifications with the set of professional qualifications associated to each personal communication device,
- the prioritization system is adapted to select the most suitable personal communication device associated to the most suitable set of professional qualifications and communicate the set of information to said personal communication device.

In one embodiment of said aspect dose the prioritization system further conduct the step of:

determines based un urgency, availability, and physical location if the set of information shall be communicated to said first or second display associated to the individual user, and communicates said set of information to said first or second display.

In one embodiment the set of communication is communicated to more than one personal communication device through the steps of:

determine the most suitable personal communication device based on the associated set of qualifications, determine a suitable personal communication device with a physical location close to the physical location where an action is required based on the set of information, wherein said suitable personal communication device is currently available, and communicate a first level of information of the set of information to a first display associated to the individual user associated to the most suitable individual user and communicate a second level of information of the set of information to a second display associated to the individual user associated to the suitable personal communication device.

The first level of information is in one embodiment detailed information about a set of information, for example an EKG curve or any other form of sensor data. The second level of information is in the same embodiment for example general information about the set of information, such as a general description of an alarm.

According to an embodiment of the prioritization system the first and second displays are arranged in different communication device associated to the same individual user.

In one embodiment is the first display a portion of a screen, in another it is the full screen.

In one embodiment of the invention the user has a communication device with more than one screen, for example a communication device comprising a first display 11 and a second display 12.

In a further embodiment of the prioritization system additional variables are added to the prioritization system in order to further improve the priority order of sets of information. For example, one additional variable could in one embodiment be information about previous sets of information communicated from a certain communication device providing a prioritization system that can adapt to changes and thereby improve how it prioritizes based on historical information from the prioritization system. In a further embodiment the historical information is the medical history of patients associated to different sensor communication devices. The person skilled in the art understands that the medical history can be both medical history collected by the prioritization system and manually, or automatically, entered information about said patient.

In one embodiment of the prioritization system are one or more algorithms used for creating a priority order.

In one embodiment of the prioritization systems can a human interact with the prioritization system and decide priority. Said human interaction can further be used as a secondarily function wherein adding human decision as one of the variables in the prioritization system.

In one embodiment of the prioritization system is the personal communication device a wearable device, such as a bracelet, clock, or any other form of device. Such a wearable device could preferably have one display, preferably the second display, arranged thereon.

In one embodiment is the first display an information presentation area.

In one embodiment of the prioritization systems is the prioritization system arranged in a back-end solution of a communication system wherein sets of information are communicated, the back-end solution comprises a list of active communication devices within said communication system. The back-end solution is adapted to perform the steps:

associating each communication device with a specific individual user, associating each communication device with a specific set of qualifications based on a professional set of qualifications corresponding to said individual user, receive at least one set of information requiring the attention of an individual user, prioritize said set of information based on urgency, categorize said set of information based on a desired set of qualifications.

match said set of qualifications for available individual users with the desired set of qualifications for said set of information, send a request to the personal communication device associated with the corresponding individual user.

In one embodiment the back-end solution further performs the step of determining the priority of the information and sending it to said first or second display.

In one embodiment of the prioritization system the prioritization system is adapted to route information between communication devises in a communication system, preferably in a care providing environment, said communication devices comprise at least one first display each and each first display is associated with one individual user, each individual user additional is associated to at least one second display wherein said first and second displays are used for different levels of information within each set of information.

The person skilled in the art further understands that said first and second display can be used for multiple sets of information simultaneously.

In one preferred embodiment of the prioritization system is the prioritization system adapted to identify the single most important set of information and communicate it to the personal communication device that is associated with the most suitable individual user based on the individual users professional set of qualifications, the physical location of said individual user, and the availability of said individual user. The most suitable individual user is in a preferred embodiment not necessary the individual user with an exact match of professional qualifications but the individual user with a combination of short response time due to availability and physical location as well as an acceptable set of qualifications to resolve the issue notified by the set of information. In a further embodiment of the prioritization system is the need for different sets of qualifications for all present sets of information evaluated and the a valuation of which individual that can be sent to which location is done based on how the total amount of sets of information are responded to with the highest level of efficiency. For this evaluation time of response, time of conducting a specific action and thereby the possibility to put sets of information on queue are evaluated in order to create an overall effective prioritization.

The prioritization system is further adapted to prioritize among levels of information comprised in each set of information. A level of information can for example be an alarm as a first level and information about the alarm as a second level. Depending on the current sets of information that are handled in the prioritization system different levels of information are communicated to said first and second displays providing a solution with multiple layers of information communication in relation to priority of information.

In one embodiment of the prioritization system is the priority system adapted to select the individual user the most suitable professional qualifications in combination with one or more criterion selected from the following:
- the distance between the position of the personal communication device and the location for the required action (i.e. the location of the origin of a set of information),
- the availability of the individual user,
- the work load of the individual user.

In one embodiment of the prioritization system is the back-end system further adapted to receive position information from at least one personal communication device associated to an individual user and use said position information to determine which personal communication device, and thereby which individual users, that is most suitable to respond to a certain set of information.

The increased amount of information communicated, possibly including for example video, live data, images, etc., in combination with the increased amount of alarms might create problems wherein the queue of information is constantly increasing and the less important issues might in a worst case scenario be postponed over and over again. This is especially relevant in situations wherein the information of a backlog to be prioritized is distributed among a plurality of individual users.

BRIEF DESCRIPTION OF DRAWINGS

The invention is now described, by way of example, with reference to the accompanying drawings, in which.

DESCRIPTION OF EMBODIMENTS

In the following, a detailed description of the different embodiments of the invention is disclosed under reference to the accompanying drawings. All examples herein should be seen as part of the general description and are therefore possible to combine in any way of general terms. Individual features of the various embodiments and aspects may be combined or exchanged unless such combination or exchange is clearly contradictory to the overall function of the prioritization system.

Briefly described the invention relates to a prioritization system in a communication network that prioritize information and communicates it to one or more communication devices with an associated to an individual user, and wherein the information is communicated through a first and second display depending on content, priority, and urgency. In a preferred embodiment of the prioritization system the communication device associated with an individual user is a personal communication device associated to an individual user.

Figure 1:
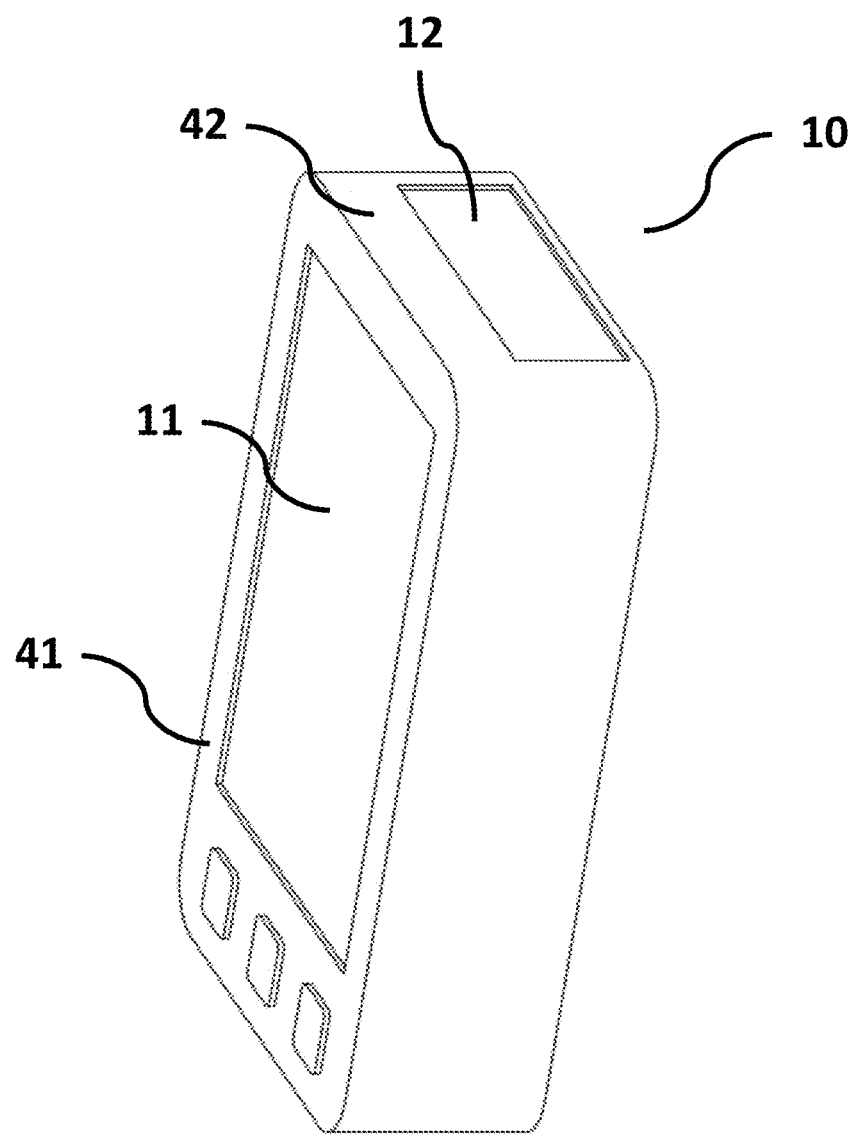
FIG. 1 illustrates a communication device in according to one embodiment of the prioritization system.

FIG. 1 illustrates a tilted isometric front/top view of a communication device 10 adapted for use with a prioritization system in a communication network. The communication device 10 comprises a first display 11 arranged on a front side 41, a second display 12 arranged on a top side 42. The first 11 and second 12 displays are displays of screen types meaning that they have the ability to show different graphical information such as numbers, symbols, characters, or any other form of graphical representation.

In one embodiment of the prioritization system is the communication device 10 that is illustrated in FIG. 1 a personal communication device 10; 10*a*; 10*b* that is associated to a specific individual user. The individual user can be any form of users, such as a professional user utilizing the personal communication device 10; 10*a*; 10*b* to receive information, technically sets of information, that are relevant for the individual users work day. In a preferred embodiment of the present invention is the individual user a user that works within any form of care providing profession, such as a doctor, nurse, or any other form of care giver.

FIG. 1 further illustrates an example of a personal communication device 10, however as will be made clear herein the personal communication device 10 comprising a first 11 and second 12 display can in another embodiment be a personal or public communication device comprising one of said screens. The other display can in one embodiment of the prioritization system be arranged on a different physical communication device as long as at least a first 11 and a second 12 display are associated to the same individual user. The individual user can in a further embodiment be associated with more than one first 11 and/or second 12 display in order to make it easier for the individual user to have constant access to the sets of information. In a preferred embodiment wherein said individual user is associated to multiple first 11 and second 12 displays are said displays synced in a way that all first displays 11 are presenting the same information and all second displays 12 are presenting the same information. I.e. different information might be presented or displayed on the first 11 and second 12 display but all first displays 11 will present the same information and the same applies for all second displays 12.

Figure 2:
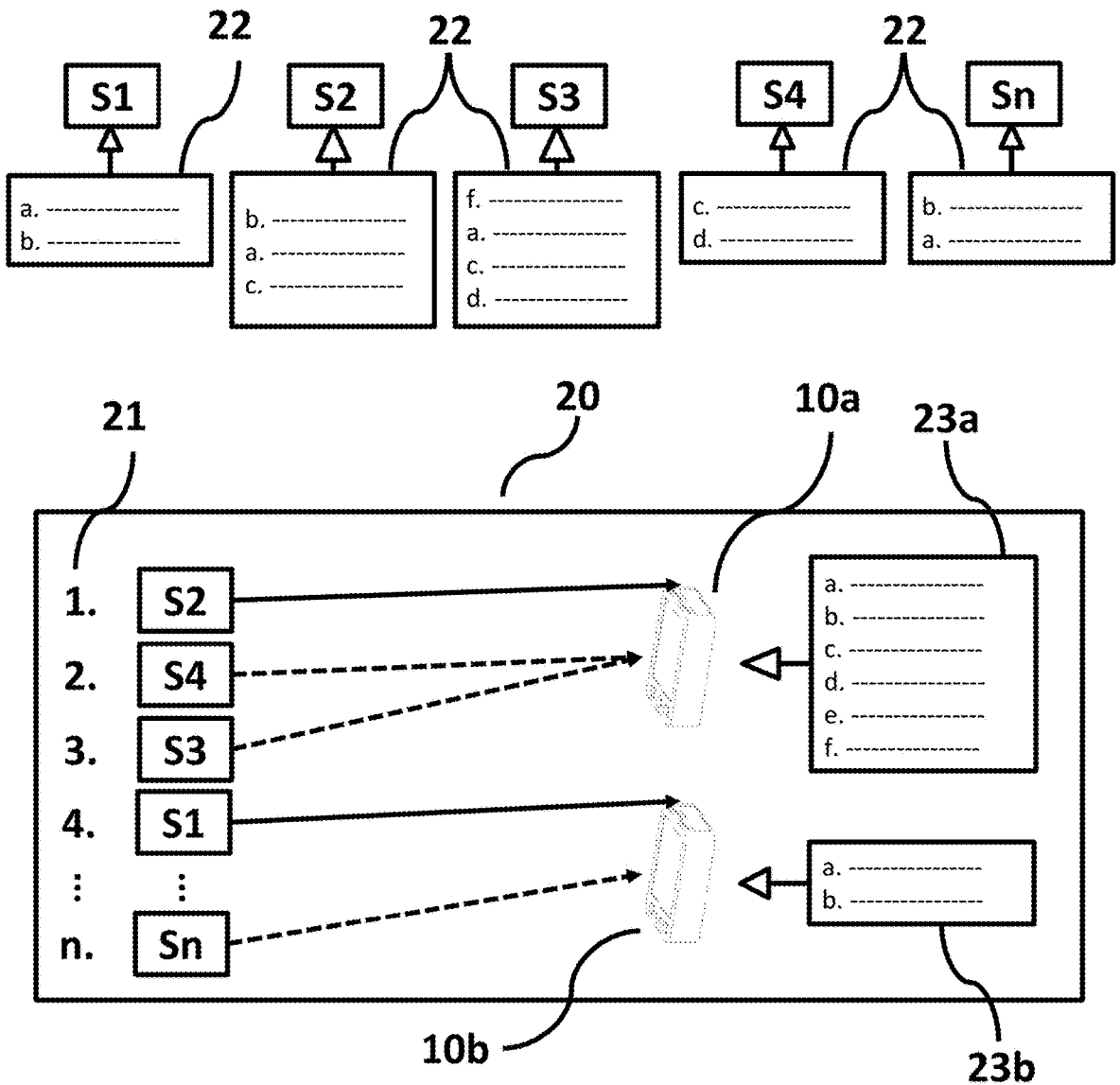
FIG. 2 illustrates a first embodiment of a prioritization system in a communication network wherein prioritization is conducted based on desired sets of qualifications.

FIG. 2 illustrates a first embodiment of a prioritization system 20 in a communication network wherein prioritizations are conducted based on desired sets of qualifications 22. The sets of information S1, S2, S3, S4, Sn can be any form and number of alarms, alerts, messages, images, videos, calls, or any other form of information addressing an issue in need of a qualified recipient, for example a healthcare professional. For the purpose of this disclosure a set of information is a set of information directed to someone for a purpose, set of qualifications, or similar, and thus not something directed to a specific person such as a direct phone call. Each set of information is associated with a desired set of qualifications 22 to be matched with a set of professional qualifications of an individual user.

The sets of information S1, S2, S3, S4, Sn, where n represent any rational number and the sets of information origins from any form of communication devices 10a, 10b in the communication network and are communicated over the communication network for prioritization by the prioritization system 20. The prioritization system 20 prioritize the sets of information S1, S2, S3, S4, Sn, depending on for example the urgency of that specific set of information S1, S2, S3, S4, Sn. Communication device 10 can for the purpose of this disclosure be any one of personal communication device, such as a tablet, PDA, or smartphone, public communication device, such as a screen, monitor, or TV, or sensor communication device such as an EKG monitor, respiratory monitor, or any other form of sensor or indication equipment that can provide alarms, tasks, or other sets of information about for example a patient automatically. The person skilled in the art understands that the communication devices 10a, 10b within one communication network can be any combination of the aforementioned communication devices 10a, 10b and any combination thereof. The sets of information S1, S2, S3, S4, Sn, are sent through the communication network and prioritized therein into a list 21 of prioritized sets of information S1, S2, S3, S4, Sn. After each set of information has been sorted into the priority order the desired set of qualifications 22 is compared to the sets of qualification 23 associated to each personal communication device 10a, 10b identifying the most suitable personal communication device 10 to transmit the set of information to. Each set of information S1, S2, S3, S4, Sn, are then communicated to one of the communication devices 10a, 10b in the prioritization order list 21. The sets of information with a transmission marked with a dashed line illustrates sets of information that are put in a queue awaiting that a set of information with higher priority shall be handled by the individual user. In one embodiment of the invention are the queued sets of information S4, S3, Sn, directly shown on the first display of respective personal communication device 10a, 10b, in one embodiment are the queued sets of information S4, S3, Sn, shown first as they are the next set of information in the priority list 21.

It should further be noted that each desired set of qualifications 22 associated to a set of information S1, S2, S3, S4, Sn have an internal priority order wherein different qualifications are considered more or less important. For example the first set of information S1 has a desired set of qualifications 22 comprising qualification a. and b. in that order. The n set of information Sn has a desired set of qualifications 22 also comprising the qualifications a. and b., however in the opposite order.

Figure 3:
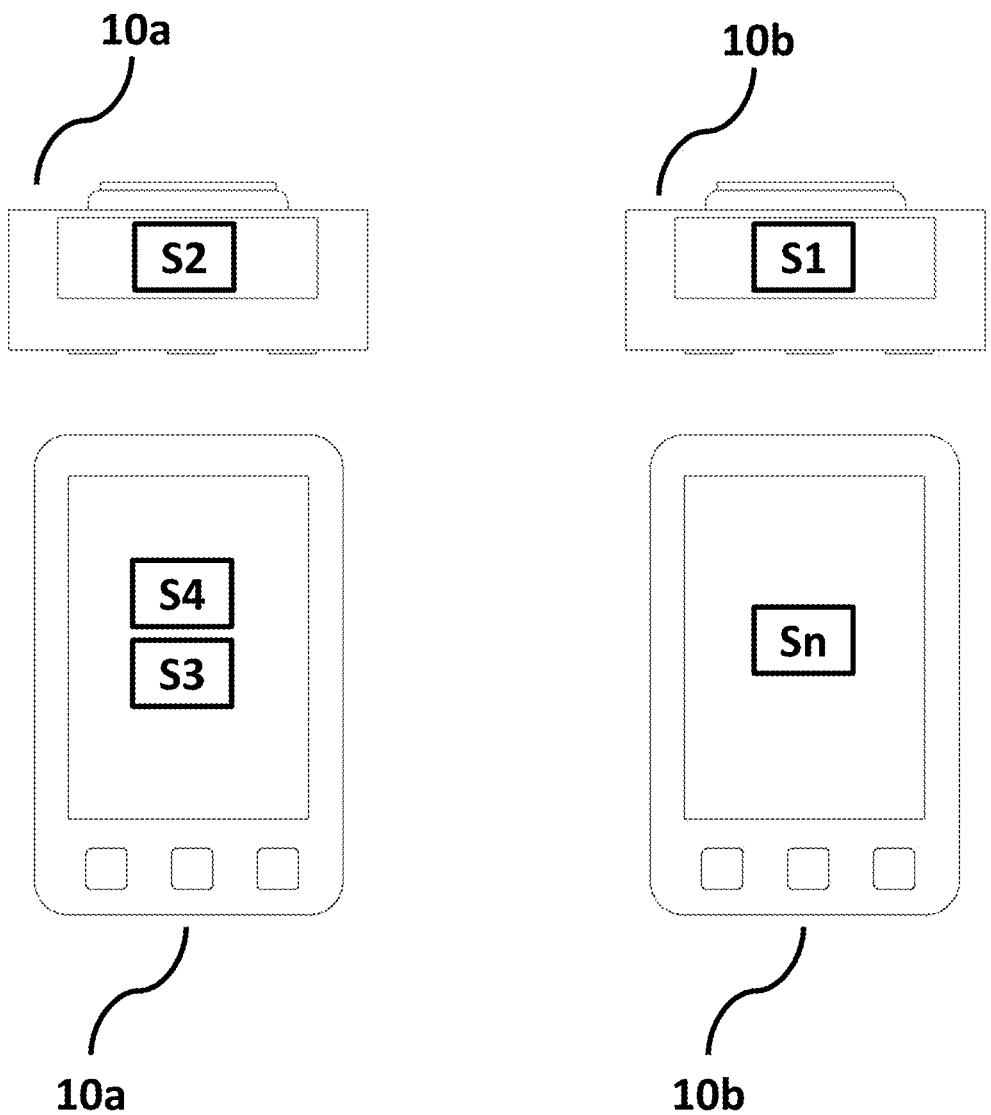
FIG. 3 illustrates two communication devices presenting sets of information according to said first embodiment of the prioritization system in a communication network.

FIG. 3 illustrates two communication devices presenting sets of information S1, S2, S3, S4, Sn, according to said first embodiment of the prioritization system 20 in a communication network. The first communication device 10a corresponds to a specific set of qualifications 23a (see FIG. 2) that are compared to the desired sets of qualifications 22 of each set of information S1, S2, S3, S4, Sn. The second communication device 10b corresponds to a specific set of qualifications 23b (see FIG. 2) that are compared to the desired sets of qualifications 22 of each set of information S1, S2, S3, S4, Sn. For said first embodiment are the qualifications 22, 23a, 23b compared on a true/false basis where all qualifications 22, 23a, 23b shall be matched in order for a specific set of informationS1, S2, S3, S4, Sn to be communicated to a specific personal communication device 10a, 10b.

The communication devices 10a, 10b can further be adapted to illustrate additional levels of information from the sets of information S1, S2, S3, S4, Sn, as will be made clear in view of for example FIGS. 8 and 13.

Figure 4:
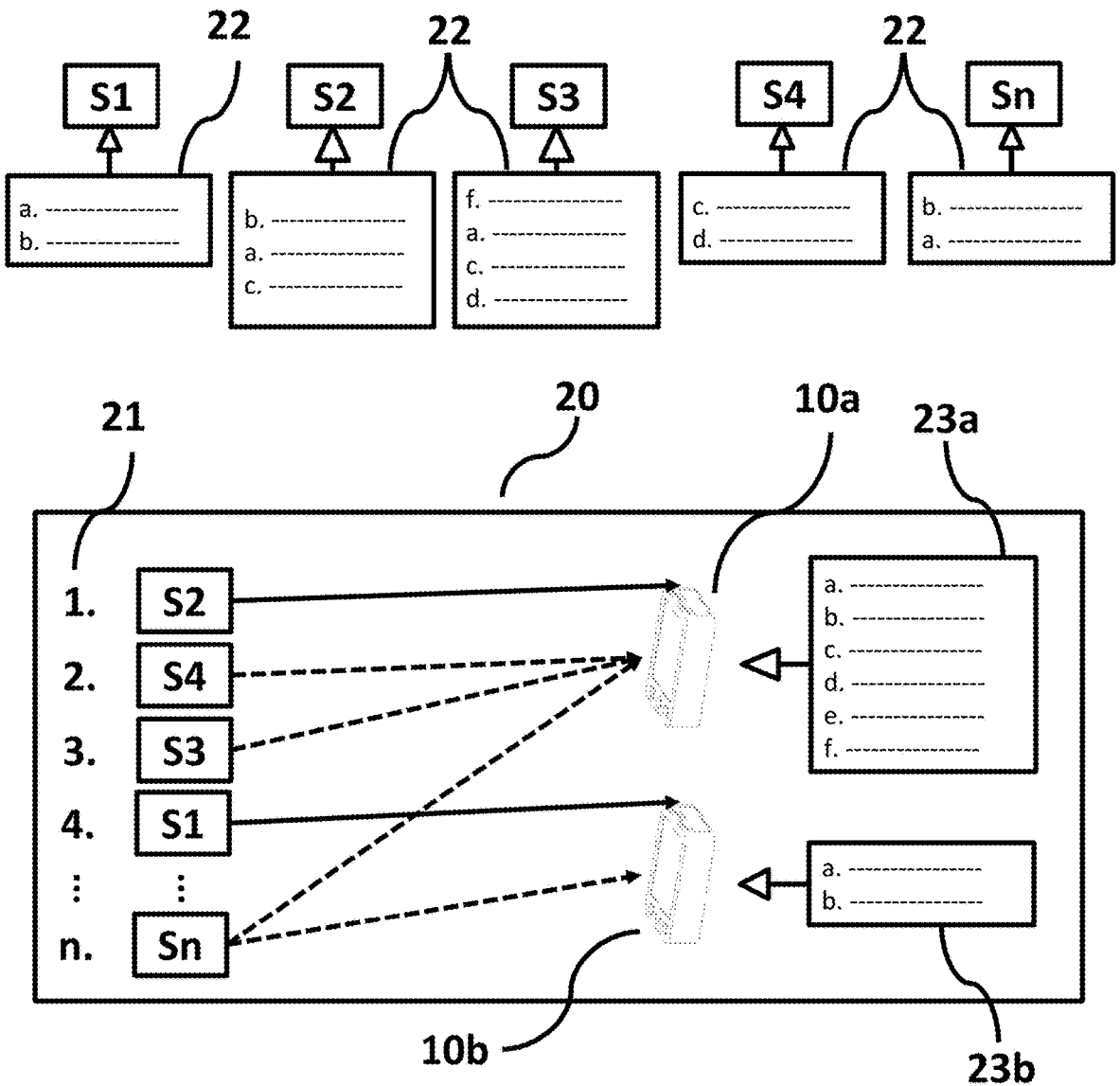
FIG. 4 illustrates a second embodiment of a prioritization system in a communication network wherein prioritization is conducted based on desired sets of qualifications.

FIG. 4 illustrates a second embodiment of the prioritization system 20 in a communication network wherein prioritizations are conducted based on desired sets of qualifications. Said second embodiment is similar to said first embodiment with the addition that each set of information, S1, S2, S3, S4, Sn, is queued for each communication device 10 and handled by the first available individual user associated to a personal communication device 10a, 10b provided that said personal communication device 10a, 10b has a corresponding set of qualifications 23a, 23b.

Figure 5:
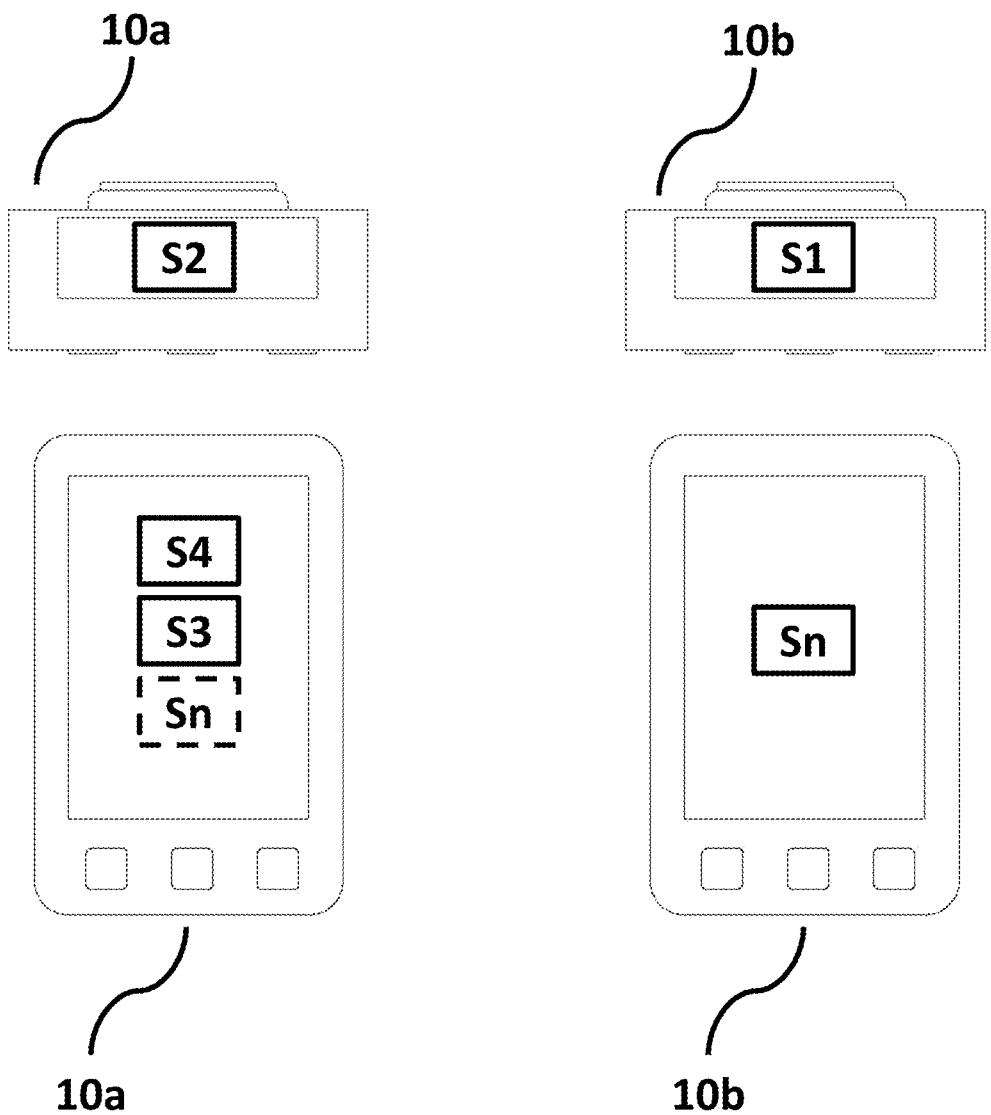
FIG. 5 illustrates two communication devices presenting sets of information according to said second embodiment of the prioritization system in a communication network.

FIG. 5 illustrates two communication devices presenting sets of information S1, S2, S3, S4, Sn, according to said second embodiment of the prioritization system 20 in a communication network. The dashed set of information Sn illustrates a set of information that will be transferred to the first communication device 10a if required, or if the individual user of the communication device 10a has completed the tasks associated with the previous sets of information S2, S4, S3 before the individual user of the communication device 10b has completed the task S1. However, as indicated in FIG. 5 the n set of information Sn is currently assigned to the second communication device 10b. In one embodiment Sn in accordance with FIG. 5 are illustrated both on the first display of the first 10a and second 10b communication devices. In another embodiment the n set of information Sn is only shown at the first display of the second communication device 10b.

Figure 6:
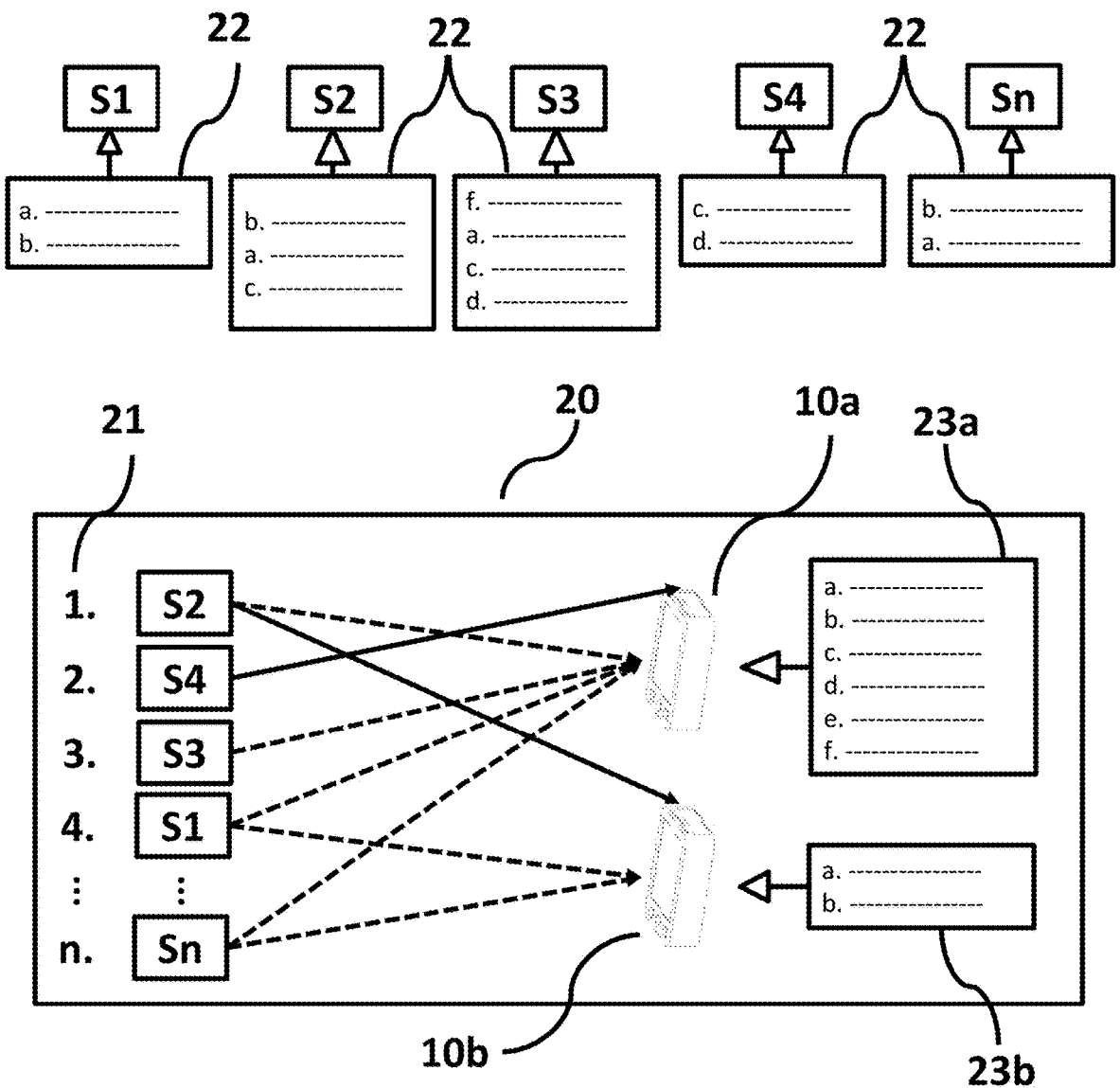
FIG. 6 illustrates a third embodiment of a prioritization system in a communication network wherein prioritization is conducted based on desired sets of qualifications and availability.

FIG. 6 illustrates a third embodiment of a prioritization system in a communication network wherein prioritization is conducted based on desired sets of qualifications 22, which of said qualifications 22 that are most important, and what other sets of information S1, S2, S3, S4, Sn, that currently requires attention. This has the effect that the prioritization is conducted a bit different than in said first and second embodiments. Thereby the sets of information S1, S2, S3, S4, Sn which are placed in a priority order list 21 and thereafter in communicated in order to at least one personal communication device 10*a*, 10*b*. For example, the second set of information S2 requests qualifications b., a., and c. which currently can only be fulfilled by the individual user associated to the first personal communication device 10*a*. However, qualification c. is considered the least relevant qualification and thereby the second set of information S2 is communicated to the second personal communication device 10*b*. Simultaneously is a backup communication comprising the second set of information S2 communicated to the first personal communication device 10*a* and placed as the next entry in the queue in case that the individual user associated to the second communication device 10*b* requires assistance. The reason for this prioritization is for example that the second most important set of information, the fourth set of information S4, requires two qualifications that only the individual user associated to the first communication device 10*a* fulfills. Additionally, those are the most important qualifications for this set of information. Thereby, the prioritization chooses to communicate the fourth set of information S4 to the first communication device 10*a* and the second set of information to the second communication device 10*b*. The person skilled in the art understands that many other priority options exist and that this is solely an example of a situation wherein the qualifications are matched for the best case scenario instead of requesting a perfect match. Furthermore, the person skilled in the art understands that in one embodiment wherein only the second set of information S2 existed would that set of information S2 be communicated to the first personal communication device 10*a* instead.

Figure 7:
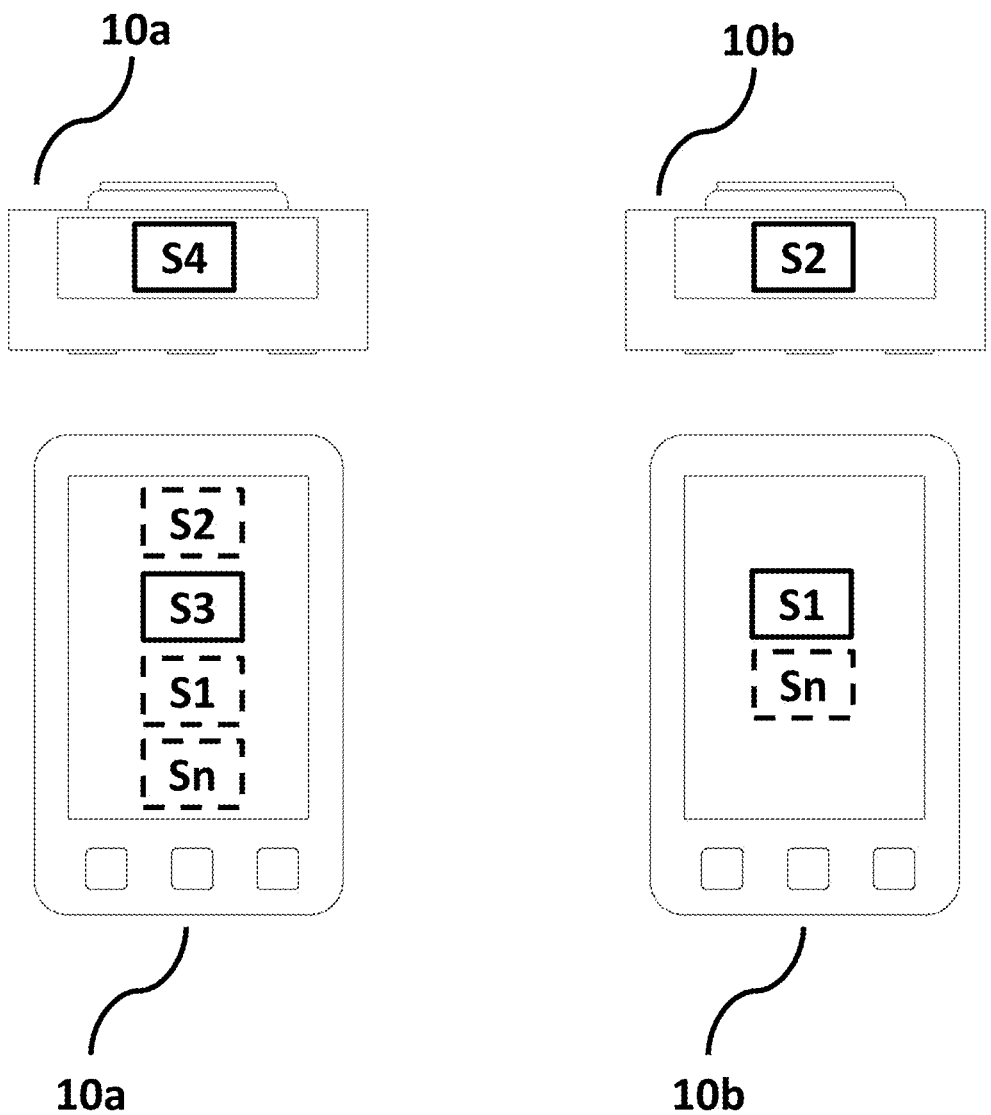
FIG. 7 illustrates two communication devices presenting sets of information according to said third embodiment of the prioritization system in a communication network.

FIG. 7 illustrates two communication devices 10*a*, 10*b* presenting sets of information S1, S2, S3, S4, Sn, according to said third embodiment of the prioritization system in a communication network. It should be noted that the queued items, S2, S1, Sn also are placed in a priority order wherein their priority might be more important even though they are communicated to multiple personal communication devices than sets of information S3 that are communicated to only one communication device.

The person skilled in the art understands that the aforementioned embodiments solely are examples and thereby not limiting to the invention as claimed in the appended claims. Said embodiments can thereby be combined in any way not contradictory to the overall function of the prioritization system.

Figure 8:
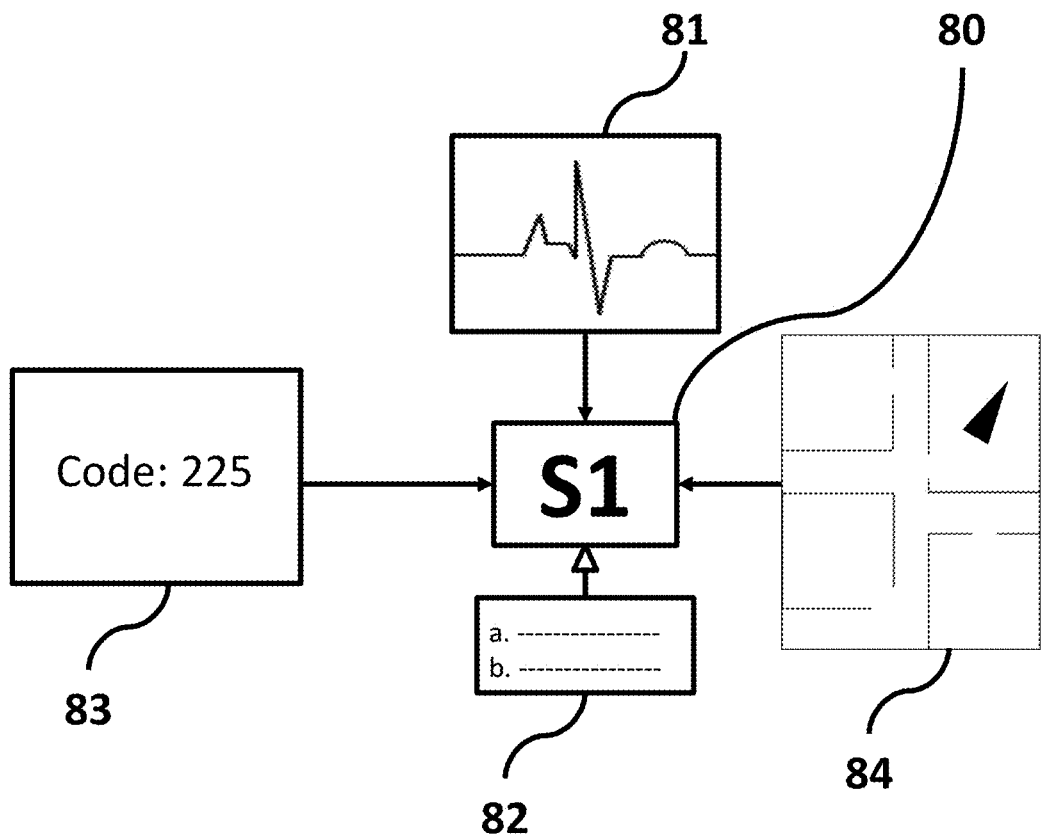
FIG. 8 illustrates one embodiment of a set of information in a prioritization system for a communication network.

FIG. 8 illustrates one embodiment of a set of information 80 in a prioritization system 20 for a communication network from a schematic view. The set of information 80 comprises multiple levels of information 81, 82, 83, 84. The levels of information 81, 82, 83, 84 in the set of information S1 are different type of information that is usable for the prioritization processes or for the individual user receiving the set of information. For example, the sets of information contains the following levels of information, the type of the set of information 83, the desired set of qualification, the location where the set of information is requesting an action to be performed 84, and information about the set of information 81, such as data on the alarm that is sent to a personal communication device.

Figure 9:
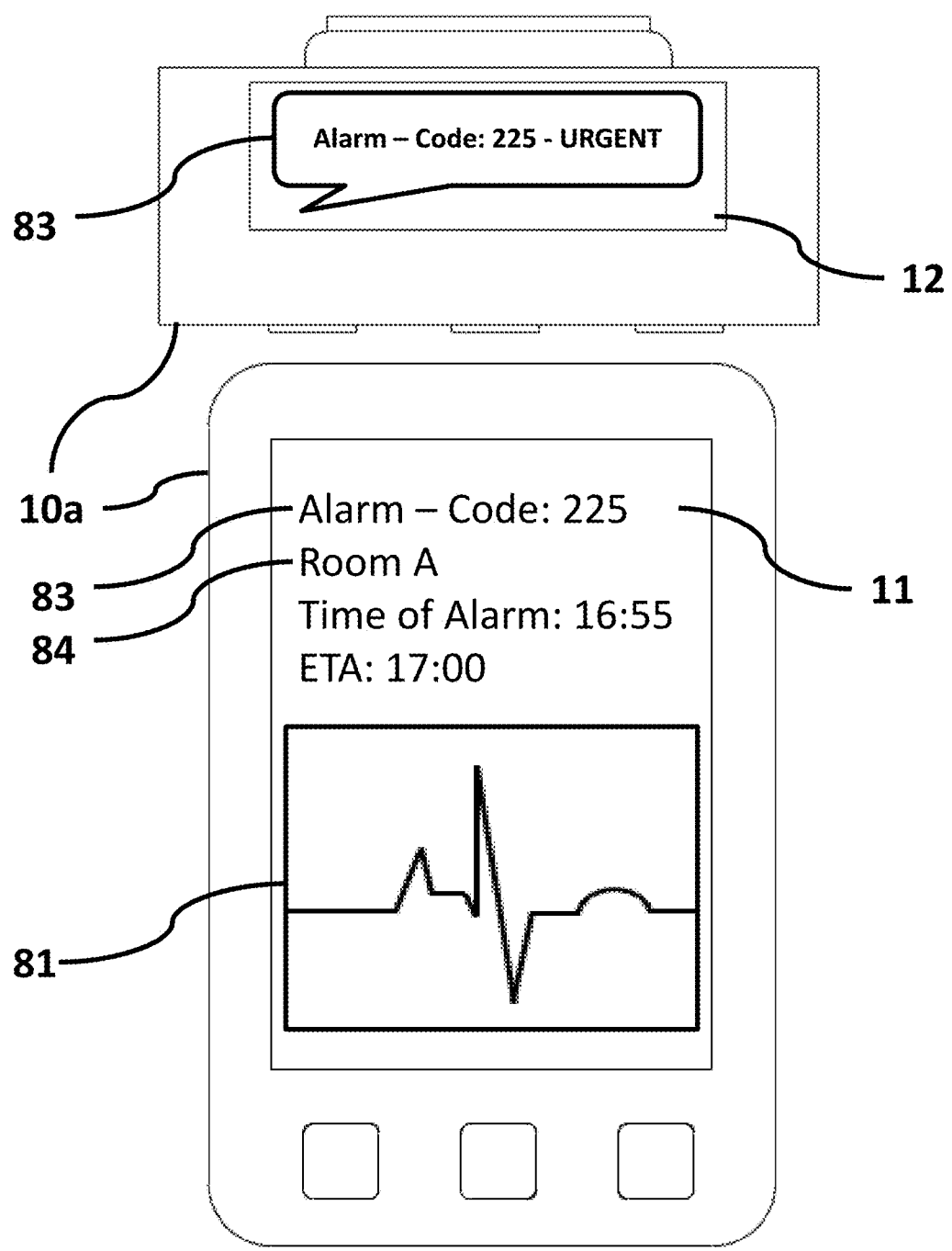
FIG. 9 illustrates a first embodiment of a communication device showing a first and second display in a prioritization system for a communication network wherein the first and second displays are arranged on the same communication device.

FIG. 9 illustrates a personal communication device 10*a* comprising a first display 11 and a second display 12 adapted to present information to an individual user associated to said personal communication device 10*a*. FIG. 9 further illustrates an embodiment of the prioritization system wherein the first 11 and second 12 displays are utilized to present different but related levels of information within a set of information communicated to a specific personal communication device 10*a*. The first display 11 is in one embodiment of the prioritization system 20, as illustrated in FIG. 9, levels of information that is part of a single set of information. The person skilled in the art understands that said levels of information 81, 82, 83, 84 can be any form of information relevant to the individual user that shall interpret a specific set of information.

Figure 10:
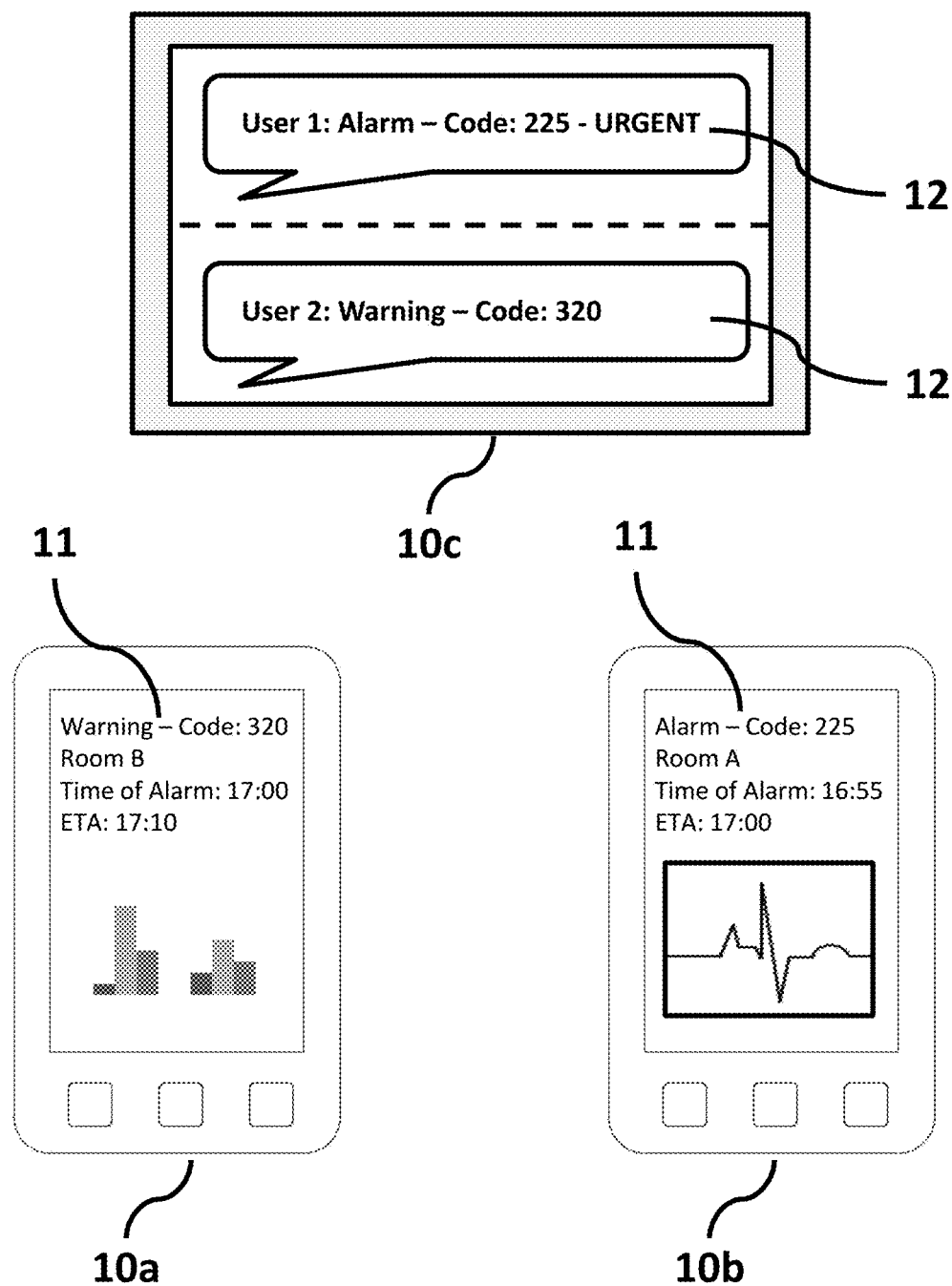
FIG. 10 illustrates a second embodiment of a communication device showing a first and second display in a prioritization system for a communication network wherein the first and second displays are arranged on different communication devices, and wherein the first display is arranged on a personal communication device and the second display is arranged on a public communication device.

FIG. 10 illustrates a second embodiment of communication devices 10*a*, 10*b*, 10*c*, showing a first and second display in a prioritization system for a communication network wherein the first 11 and second 12 displays are arranged on different communication devices 10*a*, 10*b*, 10*c*, and wherein the first display 11 is arranged on a personal communication device 10*a*, 10*b*, and the second display 12 is arranged on a public communication device 10*c*.

Figure 11:
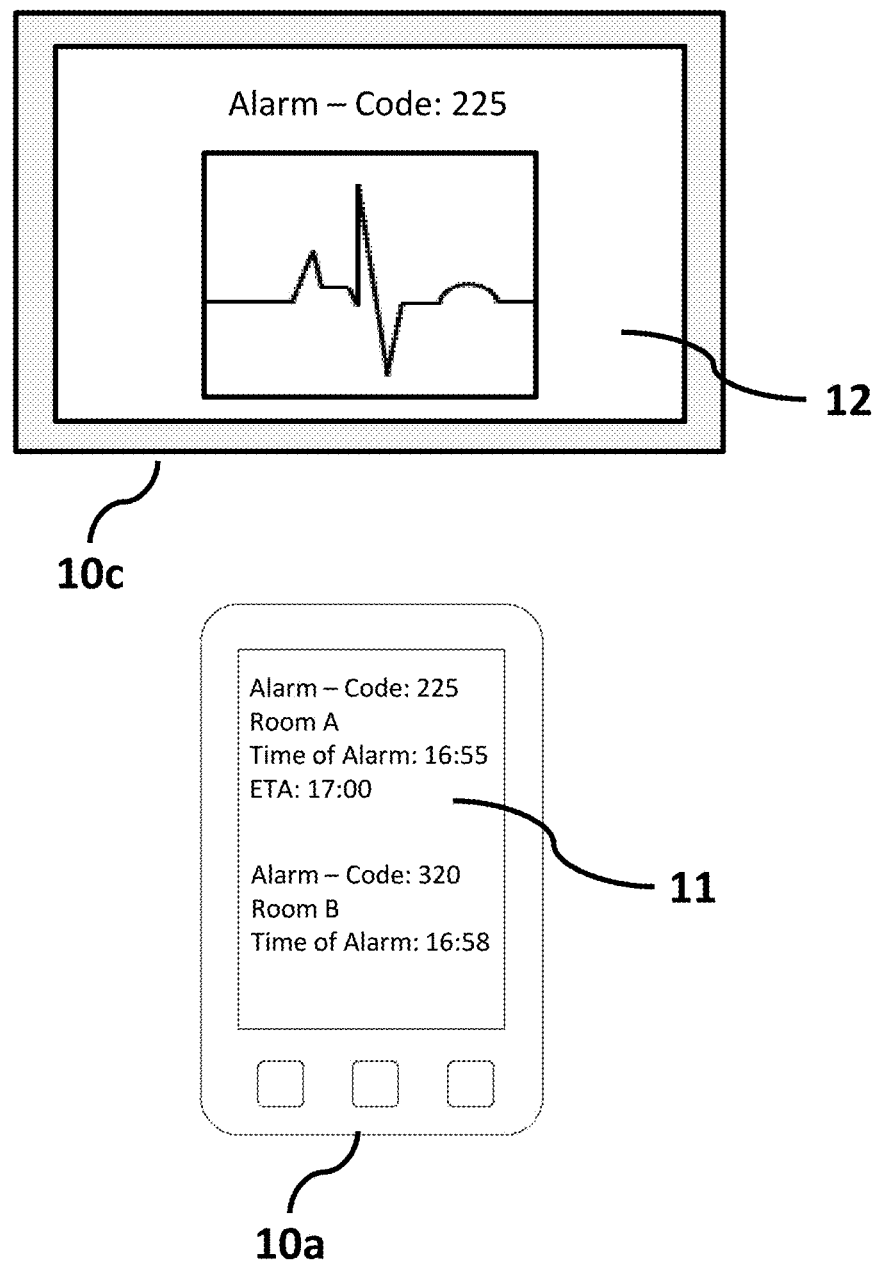
FIG. 11 illustrates a third embodiment of a communication device showing a first and second display in a prioritization system for a communication network wherein the first and second displays are arranged on different communication devices, and wherein the first display is arranged on a public communication device and the second display is arranged on a personal communication device.

FIG. 11 illustrates a third embodiment of a communication device showing a first and second display in a prioritization system for a communication network wherein the first and second displays are arranged on different communication devices, and wherein the first display is arranged on a public communication device and the second display is arranged on a personal communication device.

Figure 12:
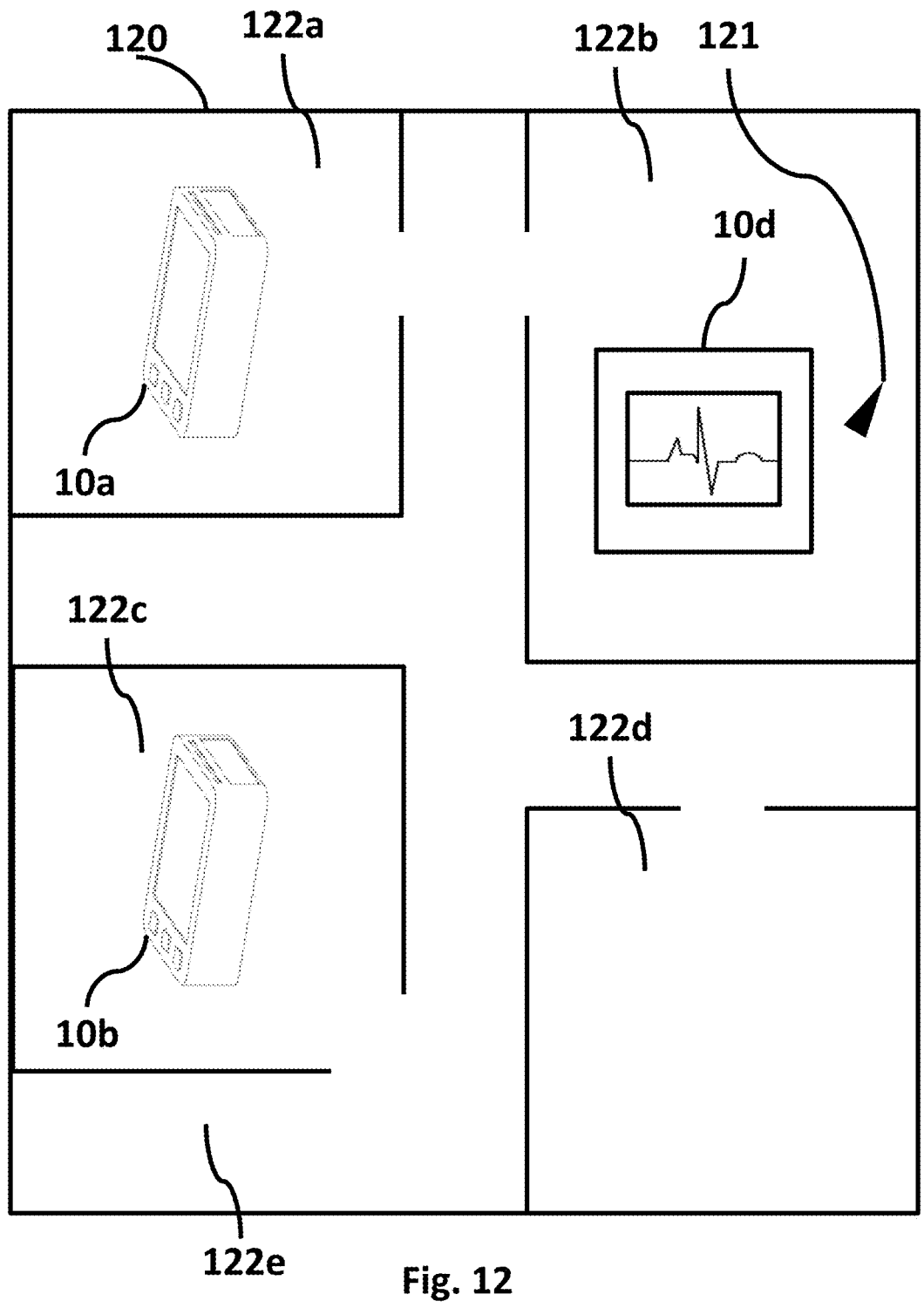
FIG. 12 illustrates an example embodiment of a prioritization system wherein physical locations of communication devices are used in the prioritization system.

FIG. 12 illustrate an example of a facility 120 wherein a prioritization system 20 is implemented. FIG. 12 further illustrates multiple rooms 122*a*, 122*b*, 122*c*, 122*d*, 122*e*, indicating different areas of said facility. Each room can for example comprise one or more communication device 10*a*, 10*b*, 10*c*, 10*d*, 10*e*, which can both send and receive sets of information. For example, a sensor communication device 10*d* can send an alarm in the form of a set of information that is prioritized and sent to a personal communication device 10*a*, 10*b*. The prioritization can for example in one embodiment comprise sets of qualifications 22, 23, physical locations 121, and the availability of the individual associated to each personal communication device 10*a*, 10*b*.

Figure 13:
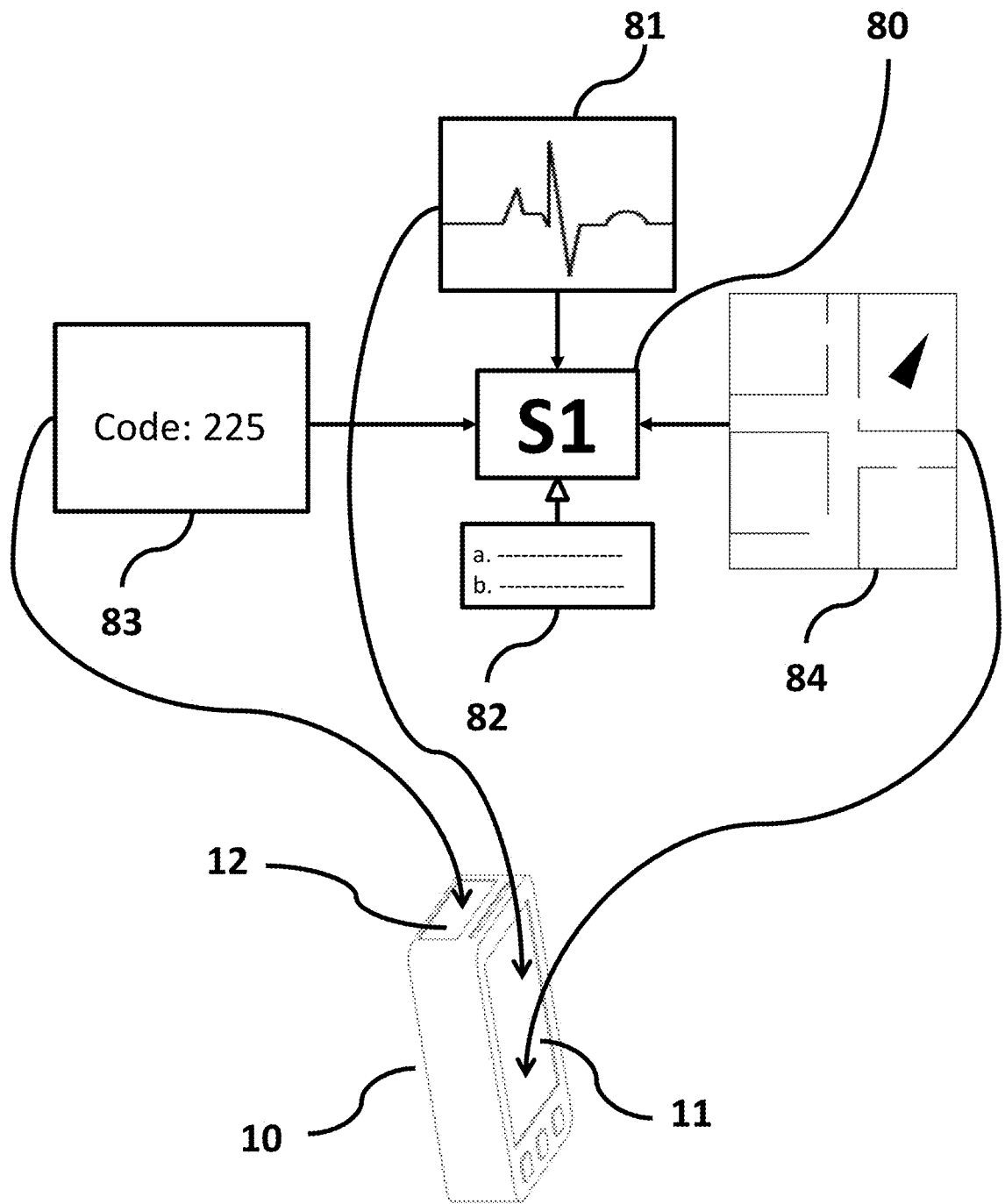
FIG. 13 illustrates a set of information with multiple levels of information that are communicated to a personal communication device.

FIG. 13 illustrates a set of information 80 with multiple levels of information 81, 82, 83, 84 that are communicated to a personal communication device 10. The different levels of information 81, 82, 83, 84 are in a preferred embodiment of the prioritization system communicated to different displays of the personal communication device 10. In this example embodiment a level of information 81 comprising sensor data for the set of information are together with the position 84 to a first screen of the personal communication device 10. The level of information 83 comprising the information that this set of information requires an immediate action is communicated to the second display 12 of said communication device.

Figure 14:
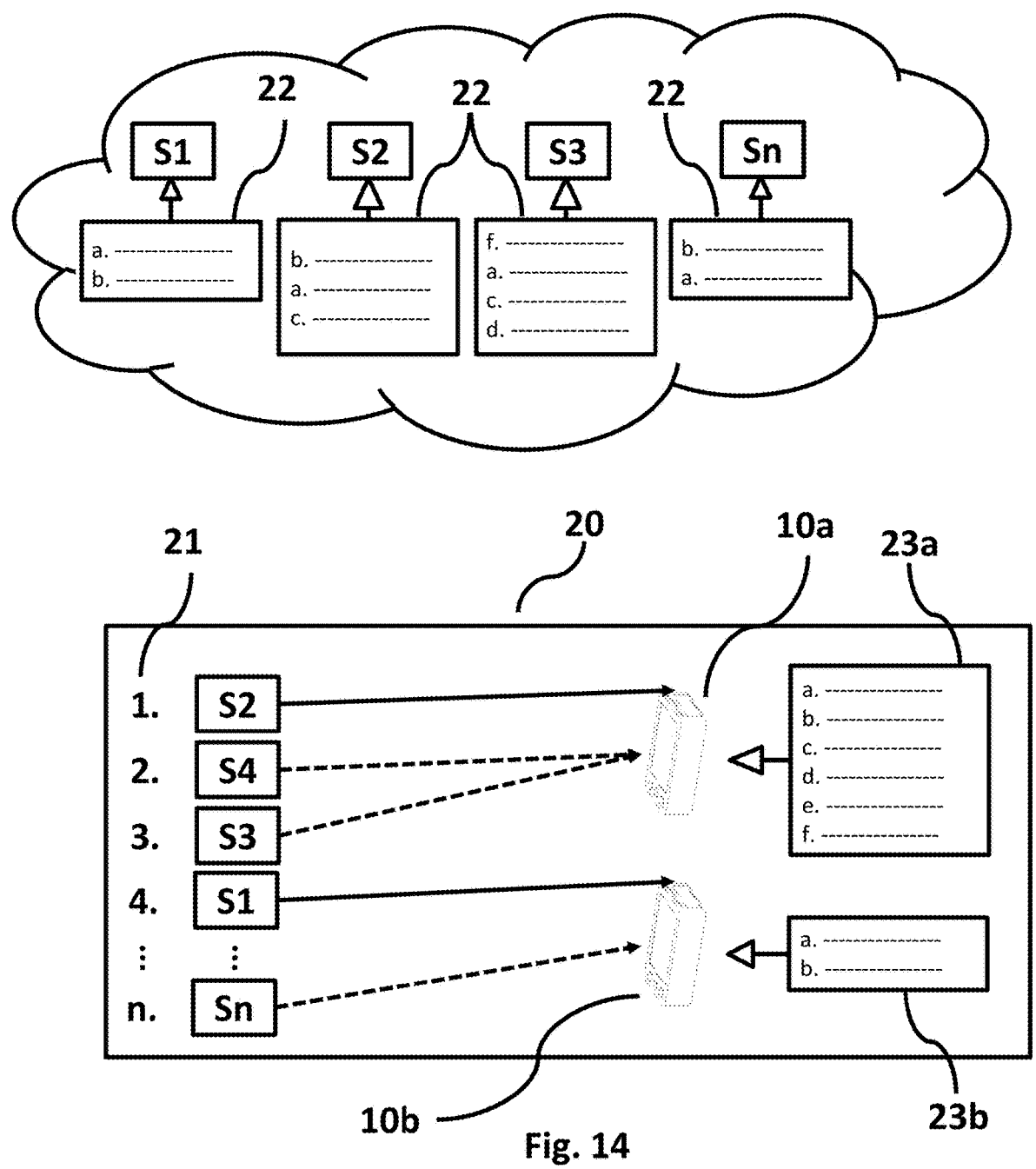
FIG. 14 illustrates a communication network comprising a prioritization system.

FIG. 14 illustrates a communication network comprising a prioritization system wherein sets of information 22 are communicated to a prioritization system 20 for prioritization. The communication network further in this example embodiment comprises communication devices 10*a*, 10*b*.

The person skilled in the art understands that the invention and the features that characterize the invention as described in the appended claims are useful in other areas than clinical environments as well. It should further be noted that in the detailed description above any embodiment or feature of an embodiment are only examples and could be combined in any way if such combination is not clearly contradictory.

The invention claimed is:

1. A prioritization system in a communication network comprising multiple communication devices adapted to communicate sets of information through said communication network, said sets of information are each associated to a level of urgency and the prioritization system is adapted to prioritize the sets of information based on said levels of urgency, wherein at least one of said communication devices is a personal communication device with a first display associated to an individual user in the prioritization system, said individual user is further associated to a second display, that has multiple associated users and displays sets of information currently intended for said multiple associated users, each personal communication device is associated to a list of qualifications in the prioritization system that are corresponding to the professional qualifications of the individual user associated to said personal communication device, each set of information communicated through said communication network is associated to a desired set of professional qualifications, the prioritization system is adapted to compare the desired set of professional qualifications with the set of professional qualifications associated to each personal communication device, the prioritization system is adapted to select the most suitable personal communication device associated to the most suitable set of professional qualifications and communicate the set of information to said personal communication device, and the prioritization system is adapted to prioritize if each set of information should be communicated to said first display associated to the individual user and/or said second display associated to said multiple users.

2. The prioritization system according to claim 1, wherein said prioritization system further is adapted to determine the availability of the individual user associated to each personal communication device, and wherein the prioritization system is adapted to additionally consider said availability when determining the most suitable personal communication device.

3. The prioritization system according to claim 1 wherein said prioritization system further is adapted to determine the physical location of each personal communication device, and wherein the prioritization system is adapted to additionally consider said physical location when determining the most suitable personal communication device.

4. The prioritization system according to claim 1, wherein said communication network is a communication network in a healthcare environment.

5. The prioritization system according to claim 1, wherein at least one of the communication devices is a public communication device, such as a monitor or TV-screen, associated to at least an individual user, preferably a team of individual users.

6. The prioritization system according to claim 1, wherein the communication network is a peer-to-peer network.

7. The prioritization system according to claim 1, wherein the prioritization system is part of a back-end system, such as a server.

8. The prioritization system according to claim 1, wherein said prioritization system further is adapted to allow a super user to manually intervene with the prioritizations, and wherein the prioritization system is adapted to additionally consider said manual interventions when determining the most suitable personal communication device.

9. A method in a prioritization system for a communication network comprising multiple communication devices adapted to communicate sets of information through said communication network, said sets of information are each associated to a level of urgency and the prioritization system is adapted to prioritize the sets of information based on said levels of urgency, wherein at least one of said communication devices is a personal communication device with a first display associated to an individual user in the prioritization system, said individual user is further associated to a second display, each personal communication device is associated to a list of qualifications in the prioritization system that are corresponding to the professional qualifications of the individual user associated to said personal communication device, each set of information communicated through said communication network is associated to a desired set of professional qualifications, the prioritization system is adapted to compare the desired set of professional qualifications with the set of professional qualifications associated to each personal communication device, the prioritization system is adapted to select the most suitable personal communication device associated to the most suitable set of professional qualifications and communicate the set of information to said personal communication device, determines based on urgency, availability, and physical location if the set of information shall be communicated to said first display associated to the individual user and/or said second display associated to multiple users, and communicates said set of information to said first or second display.

10. The method according to claim 9 wherein, the set of information is communicated to more than one personal communication device through the steps of:

determining the most suitable personal communication device based on the associated set of qualifications, determining a suitable personal communication device with a physical location close to the physical location where an action is required based on the set of information, wherein said suitable personal communication device is currently available, and communicating a first level of information of the set of information to a first display associated to the individual user and communicate a second level of information of the set of information to a second display associated to multiple users.

11. The method in a prioritization system according to claim 9, wherein said first and second displays are arranged in different communication devices associated to the same individual user.

* * * * *